United States Patent [19]
Byers

[11] Patent Number: 5,977,403
[45] Date of Patent: Nov. 2, 1999

[54] METHOD FOR THE PRODUCTION OF LOWER ORGANIC PERACIDS

[75] Inventor: Lance R. Byers, Hightstown, N.J.

[73] Assignee: FMC Corporation, Philadelphia, Pa.

[21] Appl. No.: 08/905,421

[22] Filed: Aug. 4, 1997

[51] Int. Cl.⁶ .................................................. C07F 5/02
[52] U.S. Cl. .................................................. 562/6; 562/4
[58] Field of Search ............................................. 562/4, 6

[56] References Cited

U.S. PATENT DOCUMENTS

| | | | |
|---|---|---|---|
| 2,490,800 | 12/1949 | Greenspan | 260/502 |
| 3,432,546 | 3/1969 | Oringer et al. | 260/502 |
| 4,051,058 | 9/1977 | Bowing et al. | 252/186 |
| 4,051,059 | 9/1977 | Bowing et al. | 252/186 |
| 4,297,298 | 10/1981 | Crommelynck et al. | 260/502 R |
| 5,122,538 | 6/1992 | Lokkesmoe | 514/557 |
| 5,200,189 | 4/1993 | Oakes et al. | 424/405 |
| 5,349,083 | 9/1994 | Brougham et al. | 562/6 |
| 5,368,867 | 11/1994 | Da Silva et al. | 424/616 |
| 5,508,046 | 4/1996 | Cosentino et al. | 424/616 |
| 5,720,983 | 2/1998 | Malone | 424/616 |

FOREIGN PATENT DOCUMENTS

| | | |
|---|---|---|
| 0700902 | 3/1996 | European Pat. Off. . |
| 8183766 | 7/1996 | Japan . |

OTHER PUBLICATIONS

Chemical Abstracts, 125:221197

*Primary Examiner*—Paul J. Killos
*Assistant Examiner*—J. Parsa
*Attorney, Agent, or Firm*—Patrick C. Baker; Bruce M. Monroe

[57] ABSTRACT

Dilute, aqueous solutions of lower organic peracids are rapidly prepared by reacting the anhydride of the organic acid corresponding to the peracid with concentrated hydrogen peroxide to form an aqueous peracid mixture. Before equilibrium is attained, the mixture is diluted with water and hydrogen peroxide to produce an equilibrium mixture of organic acid, peracid, hydrogen peroxide, and water. The process can be carried out in 60 minutes or less and can be run either as a batch or as a continuous process.

21 Claims, 1 Drawing Sheet

METHOD FOR THE PRODUCTION OF LOWER ORGANIC PERACIDS

TECHNICAL FIELD

This invention relates to the production of dilute, aqueous solutions of lower organic peracids. In particular, this invention relates to a rapid process for the production of dilute, aqueous solutions of lower organic peracids in which the anhydride of the corresponding organic acid is reacted with concentrated hydrogen peroxide to form a mixture that is diluted to an equilibrium mixture of organic acid, peracid, hydrogen peroxide, and water.

BACKGROUND

Dilute, aqueous solutions of lower organic peracids, especially of peracetic acid, are effective against a wide spectrum of microorganisms, including algae, fungi, bacteria, and viruses. Because they leave only the corresponding lower organic acids as residues, they are particularly suited for applications in which a non-environmentally-polluting disinfectant is required.

Dilution of concentrated solutions of organic peracids to form dilute peracid solutions is undesirable. Concentrated solutions of organic peracids not only present a risk of fire and rapid decomposition with the liberation of gases but also are a potential risk to the user due to attack on the skin and nasal mucous membranes by the peracid. Dilution also causes a disequilibrium that, over time, reduces peracid concentration and the antimicrobicidal efficiency.

An organic peracid can be formed from the corresponding acid and hydrogen peroxide by the following equilibrium reaction:

$$R-CO-OH + H_2O_2 \rightleftharpoons R-CO-OOH + H_2O \quad (I)$$

where R is an organic radical, typically a lower organic radical of 1 to 5 carbon atoms.

In dilute solutions a relatively long period of time is required to attain equilibrium because of the low concentration of the reactants. The increase in peracid concentration slows considerably as the equilibrium concentration is approached, even when concentrated solutions are used. Although an equilibrium solution containing 35% by weight peracetic acid can be prepared in about one to two days, preparation of an about 5% by weight solution of peracetic acid requires about 11 to 14 days, even in the presence of acid catalysts. Consequently, preparation of a dilute, aqueous solution of lower organic peracids by the equilibrium method is time consuming, resulting in inefficient use of plant and equipment.

Various attempts to prepare peracids have been disclosed. Greenspan, U.S. Pat. No. 2,90,800, prepared concentrated peracetic acid by reaction of concentrated hydrogen peroxide with glacial acetic acid in the presence of an acid catalyst, followed by addition of acetic anhydride to remove water.

Oringer, U.S. Pat. No. 3,432,546, discloses a process for the production of an aqueous peracetic acid solution by the reaction of hydrogen peroxide with acetic anhydride in a tubular reaction zone. However, a non-equilibrium mixture of acid, peracetic acid, hydrogen peroxide, and water, which is not suitable for storage and shipment, was produced.

Crommelynck, U.S. Pat. No. 4,297,298, discloses a process for formation of dilute solutions of organic peracids in which a concentrated solution of peracid is diluted with water and permitted to hydrolyze in the presence of an acid catalyst and then diluted with at least one of the reagents used to prepare the concentrated solution. However, this process can require up to 48 hours to attain equilibrium.

Brougham, U.S. Pat. No. 5,349,083, discloses a process in which a dilute solution having an equilibrium composition is produced by contacting concentrated hydrogen peroxide with a concentrated lower aliphatic acid to rapidly form an aqueous reaction mixture rich in peracid and diluting the reaction mixture with water and the quantities of acid and hydrogen peroxide required to reproduce the equilibrium composition of the dilute solution. Dilution is carried out before the reaction mixture has reached equilibrium. Although this process reduces the time to produce the dilute peracid solution, several hours is still required to produce a solution that contains about 21–25% by weight peracetic acid, the preferred concentration for dilution.

Thus, a need exists for a faster process for producing dilute, aqueous solutions of lower organic peracids suitable for storage and shipment.

DISCLOSURE OF THE INVENTION

Figure 1:
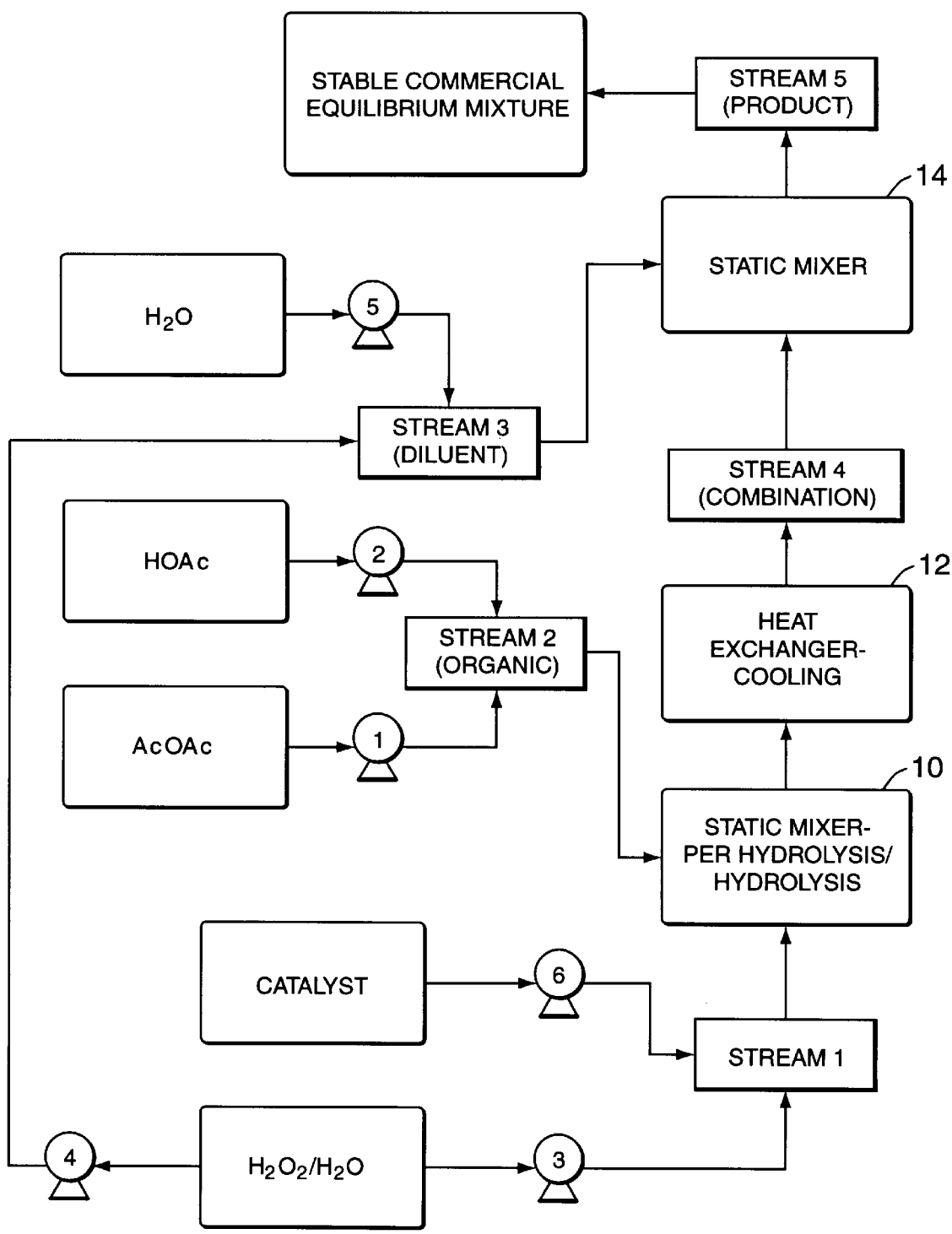
FIG. 1 is a block diagram illustrating the practice of the invention in a continuous mode.

The invention is a rapid process for the formation of dilute, aqueous solutions of lower organic peracids that does not involve a long equilibration step. A dilute, aqueous peracid solution can be produced in 60 minutes or less, typically in 30 minutes or less, as opposed to existing methods, which require hours to days to produce such solutions.

The process comprises:

(a) preparing a mixture comprising the anhydride corresponding to the lower organic peracid, hydrogen peroxide, water, an acid catalyst, and optionally the organic acid corresponding to the lower organic peracid;

(b) allowing the mixture to react for about 60 minutes or less; and (c) diluting the mixture with water, with hydrogen peroxide, and, optionally, with the organic acid to produce the dilute, aqueous solution;

wherein:

the amounts of anhydride, organic acid, hydrogen peroxide, and water used in steps (a) and (c) are effective to produce a predetermined, equilibrium concentration of the peracid;

the dilute, aqueous solution comprises about 0.5 wt % to about 15 wt % of peracid;

the concentration of the lower organic peracid in the dilute, aqueous solution produced in step (c) is about the predetermined, equilibrium concentration; and the hydrogen peroxide used in step (a) is 50 wt % to 90 wt % hydrogen peroxide in water.

The process can be run in either continuous or batch mode. A preferred lower organic acid is acetic acid.

In the practice of the invention part, or all, of the organic acid used to form the peracid in an equilibrium process is replaced with an equivalent amount of the anhydride corresponding to the organic acid. Hydrogen peroxide, the anhydride of the lower organic acid, and, typically, the organic acid corresponding to the anhydride, each of which is at a high initial concentration, are added together in the presence of an acid catalyst and allowed to react to produce the peracid. Perhydrolysis, the reaction between the anhydride and hydrogen peroxide to produce the peracid, takes place rapidly in the concentrated solutions. The reaction mixture containing the concentrated reagents is diluted with water and hydrogen peroxide before it has reached equilibrium. The resulting mixture contains a mixture of organic acid, peracid, hydrogen peroxide, and water that is at, or near, equilibrium so that there is little or no change in concentration during transport and storage.

Lower organic peracid means the peracid of an organic aliphatic monocarboxylic acid having 2 to 5 carbon atoms, such as acetic acid (ethanoic acid), propionic acid (propanoic acid), butyric acid (butanoic acid), iso-buturic acid (2-methyl-propanoic acid), valeric acid (pentanoic acid), 2-methyl-butanoic acid, iso-valeric acid (3-methyl-butanoic acid), and 2,2-dimethyl-propanoic acid. Organic aliphatic peracids having 2 or 3 carbon atom are preferred. A more preferred peracid is peracetic acid, $CH_3CO\text{—}QOH$. The dilute, aqueous solutions prepared by the process of the invention comprise about 0.5 wt % to about 15.0 wt % peracid, typically about 0.5% to about 7.0% by weight peracid, preferably about 4.0 wt % to 6.0 wt %, more preferably about 5.0% to about 5.5%

An organic acid, the anhydride derived from the organic acid, and the peracid derived from the organic acid are said to correspond to each other. Thus, acetic anhydride is the anhydride corresponding to acetic acid and peracetic acid; propionic anhydride is the anhydride corresponding to propionic acid and perpropionic acid; etc. Acetic acid is the organic acid corresponding to peracetic acid and acetic anhydride; propionic acid is the organic acid corresponding to perpropionic acid and propionic anhydride; etc. Peracetic acid is the peracid corresponding to acetic acid and acetic anhydride; perpropionic acid is the peracid corresponding to propionic acid and propionic anhydride; etc.

In step (a), the first step of the process, a mixture comprising hydrogen peroxide, the anhydride corresponding to the desired peracid, an acid catalyst, and, optionally and typically, the lower organic acid corresponding to the desired peracid, is prepared. Although the order of addition of the reagents is not important as long as they are all added at or near the same time, typically the acid catalyst is added to the hydrogen peroxide first. The organic acid and anhydride are mixed together separately and the resulting mixture then mixed with the hydrogen peroxide/catalyst mixture.

The amounts of the various reagents to be added are calculated from the final concentration of peracid desired, or predetermined, peracid concentration. The equilibrium concentration of each reagent can be calculated from the equilibrium equation (II):

$$\frac{[R\text{—}CO\text{—}OOH][H_2O]}{[R\text{—}CO\text{—}OH][H_2O_2]} = K_{ap} \qquad (II)$$

where:
[R—CO—OOH] is the concentration of peracid in mole/L;
[$H_2O$] is the concentration of water in mole/L;
[R—CO—OH] is the concentration of organic acid in mole/L;
[$H_2O_2$] is the concentration of hydrogen peroxide in mole/L; and
$K_{ap}$ is the apparent equilibrium constant for the peracid equilibrium reaction.

The apparent equilibrium constant, $K_{ap}$, is dependent on the peracid chosen and the temperature. Equilibrium constants for peracid formation are discussed in D. Swern, ed., *Organic Peroxides*, Vol. 1, Wiley-Interscience, New York, 1970. For peracetic acid at a temperature of 40° C., the apparent equilibrium constant is about 2.21. Apparent equilibrium constants at other temperatures and for other peracids can be determined by methods well known to those skilled in the art, such as, for example, by preparing a mixture containing an organic acid, hydrogen peroxide, and water; allowing it to equilibrate at the desired temperature; measuring the equilibrium concentrations of components; and calculating the equilibrium constant from the measured equilibrium concentrations.

The molar amount of hydrogen peroxide to be added to the reaction is equal to the molar amount of hydrogen peroxide in the equilibrium solution plus the molar amount of peracid in the equilibrium solution. The molar amount of organic acid quivalents to be added to the reaction mixture is equal to he molar amount of peracid in the equilibrium solution plus he molar amount of organic acid in the equilibrium solution.

The organic acid required to form the peracid can be added to the reaction mixture either as the acid or as the corresponding anhydride. Those skilled in the art will recognize that, in the calculating the reagents to be added, two moles of organic acid are equivalent to one mole of anhydride and one mole of water. The molar amount of water to be added to the reaction is equal to the molar amount of water in the equilibrium solution plus the molar amount of anhydride added to the reaction mixture. In calculating the amount of water added, care should be taken to include in the calculation the amount of water present in the aqueous hydrogen peroxide solution as well as any water that may be present in the organic acid and/or the catalyst solution.

During step (a), the first step, competing perhydrolysis and hydrolysis reactions occur. Because water is present in the hydrogen peroxide, hydrolysis of the anhydride to form the organic acid takes place:

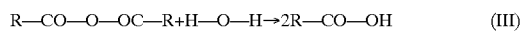

R—CO—O—OC—R+H—O—H→2R—CO—OH        (III)

Perhydrolysis is analogous to hydrolysis, except that one molecule of the anhydride reacts with one molecule of hydrogen peroxide to form one molecule of the peracid and one molecule of the acid, instead of reacting with water to form two molecules of the acid:

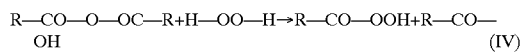

R—CO—O—OC—R+H—OO—H→R—CO—OOH+R—CO—OH        (IV)

It has been observed that perhydrolysis is more rapid than hydrolysis. Based on this discovery, it is possible to form significant amounts of peracid from an anhydride by the process of this invention, even in the presence of significant amounts of water.

The hydrogen peroxide added to step (a) is typically about 50% to 90% aqueous hydrogen peroxide. Although solutions containing other amounts of hydrogen peroxide in water can be used, 70% aqueous hydrogen peroxide is preferred because it is commercially available and gives reasonably short reaction times. It also provides water for the competing hydrolysis reaction. If less concentrated hydrogen peroxide solutions are used, longer reaction times may be required, and it may be necessary to increase the amount of anhydride added and decrease the amount of organic acid added correspondingly. If 70% hydrogen peroxide is added during step (a) and a hydrogen peroxide/water mixture is added in step (c), the dilution step, the mixture added during step (c) is typically about 20–30 wt % hydrogen peroxide. For solutions containing about 5.0 wt % to 5.5 wt % peracetic acid, 25 wt % hydrogen peroxide is preferred.

Only a portion of the hydrogen peroxide is added in step (a) so that the concentration of anhydride is relatively high during this step. If all the hydrogen peroxide were added during step (a), the concentration of anhydride would be relatively lower and the concentration of water relatively higher during this step. Typically, about 5% to 40%, preferably 10% to 35%, more preferably about 15% to 30%, of the total hydrogen peroxide used in the process is added during step (a).

The anhydride is preferably essentially 100%, if available. The organic acid is preferably at least 90% organic acid. When peracetic acid is prepared, acetic anhydride and glacial acetic acid (about 99.5% acetic acid) are preferred.

Moles of organic acid equivalents added is equal to the sum of the number of moles organic acid added plus twice the number of moles of anhydride added. The ratio of the moles of organic acid equivalents added to moles of hydrogen peroxide added will depend on the desired predetermined equilibrium peracid concentration, which can be calculated as described above. However, for dilute aqueous solutions of peracid, especially for peracetic acid, this ratio is typically about 1.4 to 1.8, preferably about 1.5 to 1.7, more preferably about 1.6. To prevent formation of an explosive mixture using 70% peroxide in the peracetic acid reaction, this ratio should never be less than 1.25. If more or less concentrated hydrogen peroxide is used, this limit will be higher or lower, respectively. For reactions forming higher molecular weight peracids, this lower limit will be different, due to the higher molecular weight of the acids.

As noted above, the total amount of organic acid and anhydride added to the reaction mixture depends on the desired, predetermined equilibrium peracid concentration. For efficient peracid formation from the anhydride, essentially all the anhydride should be added in step (a). Anhydride added after step (c), the dilution step, will primarily undergo hydrolysis, rather than perhydrolysis, because of the much higher concentration of water after dilution.

All the organic acid can be added in step (a) or in step (c), or part can be added in step (a) and part in step (c). Although a major amount of the peracid formed during step (a) is formed by reaction of the anhydride with concentrated hydrogen peroxide, the organic acid also reacts with the concentrated hydrogen peroxide to form the peracid.

Because hydrogen peroxide reacts much more rapidly with the anhydride than with the organic acid, the rate of peracid formation can be controlled by controlling the concentration of organic acid and the concentration of the anhydride in the reaction mixture. The ratio of organic acid to its corresponding anhydride added in step (a) determines the concentration of organic acid and the concentration of the anhydride in the reaction mixture. This ratio depends on a number of factors: the temperature, the concentration of catalyst, and the concentrations of anhydride, organic acid and hydrogen peroxide in the reaction mixture, and the desired reaction time for step (a). For ease of operation, it is typically convenient to add all of the organic acid in step (a).

A catalyst is required for equilibrium to be reached in the minimum time. Suitable catalysts are strong mineral or organic acids, such as sulfuric acid, sulfonic acids, and phosphonic acids. The catalyst is typically 0.5 wt % to 10 wt % of the reaction mixture; typically 1 wt % to 5 wt % of the reaction mixture.

The dilute, aqueous solution typically, and preferably, contains a stabilizer. The stabilizer is a sequestering agent that chelates metals which catalyze the decomposition of hydrogen peroxide. These materials are well known to those skilled in the art and, include, for example, pyridine carboxylates, such as dipicolinic acid, and organic phosphonic acids capable of sequestering bivalent metal cations, as well as the water-soluble salts of such acids.

Organic phosphonic acids are preferred, because they can also catalyze both the perhydrolysis and the hydrolysis reactions. Preferred phosphonic acids are low molecular weight aliphatic compounds containing at least two acidic groups, at least one of which is a phosphonic acid. A particularly preferred stabilizer is 1-hydroxyethylidene-1,1-diphosphonic acid, which is sold as Dequest® 2010 stabilizer. Although the stabilizer can be added either during or after dilution, it is preferably added during step (a) (the perhydrolysis/hydrolysis reaction) and, thus, functions as both a catalyst and a stabilizer.

The water should be free from metal ions that would catalyze decomposition of hydrogen peroxide, such as ferrous ions, ferric ions, cupric ions, cuprous ions, and similar transition metal ions. The water is also preferably free from organic material that would be oxidized by the peracid. Distilled or deionized water is preferred.

Diacyl peroxides can be formed during the reaction. Diacyl peroxides are not formed in the initial reaction between the anhydride and hydrogen peroxide. They are secondary reaction products, formed by reaction of the as yet unreacted anhydride with the initially formed peracid:

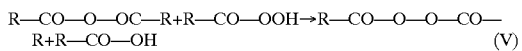
$$R\text{—}CO\text{—}O\text{—}OC\text{—}R+R\text{—}CO\text{—}OOH \rightarrow R\text{—}CO\text{—}O\text{—}O\text{—}CO\text{—}R+R\text{—}CO\text{—}OH \quad (V)$$

Consequently, diacyl peroxides do not begin to accumulate in solution until a significant amount of peracid has been formed.

Although diacyl peroxides are known to be explosive in pure, crystalline form, dilute, aqueous solutions of diacyl peroxides, such as solutions of 1 wt % or less of diacetyl peroxide in water, are not explosive. Because dilution decreases the concentration of reactants and hydrolyses the remaining anhydride to the corresponding acid, formation of diacyl peroxide essentially ceases once the reaction mixture is diluted. Following step (c), any diacyl peroxide in the reaction mixture is irreversibly hydrolyzed to acid and peracid.

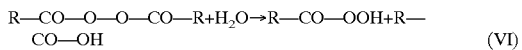
$$R\text{—}CO\text{—}O\text{—}O\text{—}CO\text{—}R+H_2O \rightarrow R\text{—}CO\text{—}OOH+R\text{—}CO\text{—}OH \quad (VI)$$

Because the reaction mixture is diluted only a few minutes after the reagents are mixed, the diacyl peroxide concentration in the reaction mixture typically does not exceed about 0.8 wt % or less. After several days, no detectable diacyl peroxide remains in the reaction mixture.

The process can be run as either a batch or continuous process.

In the batch process, hydrogen peroxide, the anhydride, the acid catalyst, and, typically, the organic acid, are mixed and allowed to stand. The time for which the reaction mixture is allowed to stand depends on a number of factors: the temperature, the concentration of catalyst, the ratio of anhydride to organic acid, and the concentrations of anhydride, organic acid and hydrogen peroxide. Typically, about 60 minutes or less is adequate to produce the peracid concentration appropriate for dilution in step (c). When 70% hydrogen peroxide is used to produce a final solution that has an equilibrium peracetic acid concentration of about 5.0 wt % to 5.5 wt %, the reaction mixture is allowed to stand for about 5 to 30 minutes, preferably about 10 to 20 minutes, more preferably about 15 minutes.

The reaction of step (b) may be carried out at a temperature between the freezing point of the reactants and 60° C., preferably between about ambient and about 50° C., more preferably between about 30° C. and about 50° C., most preferably about 40° C. To prevent decomposition of the hydrogen peroxide, the reaction temperature normally should not exceed 60° C. for more than a brief period of time. Because the perhydrolysis and hydrolysis reactions are exothermic, cooling may be required to control the temperature.

Before the system containing the concentrated reagents reaches equilibrium, water and the balance of the hydrogen peroxide are added. Additional organic acid may be added if necessary to produce the predetermined, equilibrium concentration of organic acid. If the appropriate amount of each reagent is added initially, if the reaction mixture is allowed to stand for the appropriate time before dilution, and if the reaction is diluted by the appropriate amount of each reagent, an essentially equilibrium mixture, with the predetermined equilibrium peracid concentration, is produced on dilution.

In the continuous process, hydrogen peroxide, the anhydride, the acid catalyst, and, typically, the organic acid, are introduced into a mixer in step (a) to produce a reactant stream. During step (b), the reactant stream passes through the mixer. During step (c), water, the balance of the hydrogen peroxide, and, optionally, organic acid, are added to the reactant stream at the appropriate time, preferably in a second mixer.

In a preferred embodiment of the continuous process three process streams are combined in two discrete sections or stages. The production of peracetic acid will be described. However, it will be understood that dilute solutions of other lower organic peracids similarly can be produced in a continuous process by replacing acetic anhydride and acetic acid with the appropriate anhydride and organic acid.

The first stream (stream one) contains a portion of the ydrogen peroxide and all of the catalyst. The reagents can be premixed and added from a reservoir as a single stream, or he stream can be formed by mixing a hydrogen peroxide stream and a catalyst stream immediately prior to reaction.

The second stream (stream two) contains the acetic anhydride and glacial acetic acid, if present, in the desired ratio. The reagents can be premixed and added from a reservoir as a single stream, or the stream can be formed by mixing an acetic acid stream and a glacial acetic acid stream immediately prior to reaction. Alternatively, a stream of water and a stream of acetic anhydride can be combined to produce a stream containing the desired ratio of acetic anhydride to acetic acid. The first and second streams are mixed in the first stage of the reaction, corresponding to step (a).

The third stream (stream three), which contains the remainder of the hydrogen peroxide and the remaining water, is added during the second stage of the reaction. The reagents can be premixed and added from a reservoir as a single stream, or the stream can be formed by diluting a stream of concentrated hydrogen peroxide with a stream of water immediately prior to reaction.

An additional stream, containing acetic acid, can also be added during the second stage of the reaction if it is necessary to add acetic acid to produce the predetermined, equilibrium concentration. This stream can be added directly to the mixer or premixed with the hydrogen peroxide/water stream shortly before addition. If the acid is added to the hydrogen peroxide hours to days before addition, considerable peracid may be formed by the equilibrium reaction so that the predetermined, equilibrium concentration is not attained on dilution.

Referring to FIG. 1, section one (stage one) comprises mixer 10 and heat exchanger 12 . Calibrated pumps 1–6 deliver each of the reagent streams to the reaction. To carry out step (a) of the process, stream one and stream two are combined directly upstream from mixer 10 . Mixer 10 provides efficient mixing for the reactants. Heat exchanger 12 provides the necessary cooling for the exothermic perhydrolysis/hydrolysis reaction. In an alternate embodiment (not shown) mixer 10 and heat exchanger 12 are combined in a mixer-heat exchanger combination by, for example, placing the heat exchanger around the mixer.

Mixers and heat exchangers are well-known to those skilled in art. Mixers include, for example, static mixers and paddle mixers. Heat exchangers include tube in tube heat exchangers, multitube heat exchangers, and the like.

The perhydrolysis/hydrolysis reaction is carried out at a temperature between the freezing point of the reactants and 60° C., preferably between about ambient and about 50° C., more preferably between about 30° C. and about 50° C., most preferably about 40° C. To prevent decomposition of the hydrogen peroxide, the reaction temperature should not exceed 60° C. Because the perhydrolysis and hydrolysis reactions are exothermic, cooling will typically be required to maintain this temperature.

The residence time in section one depends on the ratio of acetic anhydride to acetic acid and the concentrations of acetic anhydride, acetic acid and hydrogen peroxide. With 70% hydrogen peroxide at 40° C. the residence time is about 5 to 60 minutes, preferably about 10 to 20 minutes. About 15 minutes is most preferred. Step (b) of the process is accomplished as the reactant stream passes through mixer 10 and heat exchanger 12. The residence time in section one is the time for which the mixture is allowed to react in step (b). Section two (stage two) comprises mixer 14. Step (c) is accomplished by combining stream 4, the reactant stream exiting stage 1, with stream 3, either at the exit from stage one or in mixer 14 and passing the resulting flow through stage two.

Heating or cooling during stage two is generally not necessary. The temperature will typically range between the ambient temperature and the temperature of stage one.

Although longer residence times may be used, the residence time in section two need be only long enough to produce mixing of the added reagents. If the appropriate amount of each reagent is added in stage one, if the reaction mixture has the appropriate residence time in stage one before dilution, and if the reaction is diluted by the appropriate amount of each reagent in stage two, an essentially equilibrium mixture, corresponding to the desired, predetermined equilibrium mixture, is produced on dilution.

Stream 5, the flow exiting stage two, contains about the desired predetermined equilibrium peracid concentration. It can be used immediately or stored and shipped without undergoing a significant change in peracid concentration during storage and shipment.

INDUSTRIAL APPLICABILITY

Dilute, aqueous solutions of lower organic peracids are effective against a wide spectrum of microorganisms, including algae, fungi, bacteria, and viruses. Because they leave only the corresponding lower organic acids as residues, they are particularly suited for applications in which a non-polluting disinfectant is required, for both industrial disinfection and domestic use. For example, these solutions are widely used in the pulp and paper industry to prevent the growth of microorganisms during the production of paper. They are also used to prevent the growth of microorganisms in cooling towers. These solutions can also be used in applications in which a non-polluting strong oxidant is required, such as textile bleaching.

The advantages of the invention will be apparent from the following examples, which illustrate, but do not limit, the invention.

EXAMPLES

| | Glossary |
|---|---|
| AA | Acetic anhydride |
| DAP | Diacetyl peroxide |
| Dequest ® 2010 | Stabilizer containing 60 wt % 1-hydroxy-ethylidene-1,1-diphosphonic acid; 3 wt % phosphonic acid, and 37 wt % water (Monsanto, St. Louis, MO) |
| HOAc | Glacial acetic acid |
| PAA | Peracetic acid |

Comparative Example

This example illustrates formation of a dilute solution of peracetic acid by a process similar to that disclosed in Brougham, U.S. Pat. No. 5,349,083.

A 100 mL passivated, jacketed glass reaction vessel was brought to 40° C. by circulating water from a temperature controlled circulating water bath through the jacket. The following reagents were added to the reaction vessel, in the order given:

| | |
|---|---|
| Glacial acetic acid | 13.962 g |
| Dequest ® 2010 | 1.049 g |
| Hydrogen peroxide (70 wt %) | 6.973 g |

The reaction was stirred at 40° C. for 207 min using a magnetic stirrer and a Teflon® perfluorinated resin coated magnetic stirring bar. Then a mixture of deionized water (50.446 g) and 70 wt % hydrogen peroxide (27.560 g) was added to the reaction mixture.

The reaction mixture was analyzed using the standard differential analytical procedure (D. Swern, ed., *Organic Peroxides*, Vol. 1, Wiley-Interscience, New York, 1970, p. 501). The sample was titrated with ceric sulfate solution at about 0° C. to determine hydrogen peroxide. Excess potassium iodide solution is then added. The resulting solution is back titrated with sodium thiosulfate at about 0° C. to determine peracid. The resulting solution is warmed on a steam bath to hydrolyze the diacetyl peroxide to peracid and titrated with additional sodium thiosulfate to determine diacetyl peroxide. Because diacetyl peroxide is determined from the difference of three titrations, the error in the diacetyl peroxide concentration is about 0.2 wt %.

The resulting solution contained 5.39 wt % peracetic acid and 22.25 wt % hydrogen peroxide. Diacetyl peroxide was not determined for this example because its formation is not expected under these conditions.

The reagents charged should produce a final equilibrium mixture containing about 5 wt % peracetic acid. If all the reagents were added at the same time and the reaction mixture were maintained at about 40° C., about 4 to 6 days would be required to reach a near equilibrium peracetic acid concentration of about 5.1 wt %. If the reaction mixture were maintained at about 20° C., about 11.5 to 14 days would be required to reach a near equilibrium peracetic acid concentration of about 5.1 wt %. In this process, a concentration of 5.39 wt % peracetic acid was attained in 207 minutes (0.144 day). Although this concentration slightly exceeds the equilibrium concentration, it decreases to the equilibrium concentration on standing.

EXAMPLE 1

This example illustrates production of a dilute solution of peracetic acid by using a mixture of acetic acid and acetic anhydride in a batch process.

The procedure of the Comparative Example was repeated, except that the following reagents were added to the glass reaction vessel, in the order given:

| | |
|---|---|
| Deguest ® 2010 | 1.051 g |
| Hydrogen peroxide (70 wt %) | 6.972 g |

Acetic anhydride (9.869 g) and glacial acetic acid (2.357 g) were combined and added over the course of 1 min. The reaction mixture rose to about 70° C. After an additional 5 min, a mixture of deionized water (52.224 g) and 70 wt % hydrogen peroxide (27.560 g) was added to the reaction mixture. The reaction mixture was analyzed by the procedure described in the Comparative Example. It contained 5.13 wt % peracetic acid and 23.08 wt % hydrogen peroxide. Diacetyl peroxide was not determined for this example.

The total reagents charged should produce a final equilibrium mixture containing about 5 wt % peracetic acid. In this process, a solution with the concentration of 5.13 wt % peracetic acid was produced in about 6 minutes (0.0042 day). This concentration is essentially the equilibrium concentration of about 5.1 to 5.3 wt % peracetic acid.

EXAMPLE 2

This example illustrates production of a dilute solution of peracetic acid by using a mixture of acetic acid and acetic anhydride in a continuous process.

The continuous reaction was carried out in a two section reactor. Section one consists of a central 9.25 in (about 23.5 cm) long by 0.25 in (about 0.64 cm) diameter 316 stainless steel static mixer with 27 internal helical mixer elements. On the outside of the static mixer was constructed a tube-in-tube heat exchanger using 0.375 in (about 0.95 cm) 316 stainless steel tubing and appropriate Swagelok® bored-through tees. On the ends of the static mixer are Swagelok® crosses to provide for input and exit streams and temperature probes, if desired. A concentric injection tube was constructed such that mixing of the hydrogen peroxide/catalyst stream and the acetic acid/acetic anhydride stream occurs very near to, and upstream from, the static mixer. Temperature control was provided by circulating water from a temperature controlled circulating water bath through the heat exchanger. The total internal volume of the static mixer is 5.1 mL. Good mixing and heat exchange are provided by this apparatus.

Section two of the reactor is a 7.0 in (about 17.8 cm) long by 0.25 in (about 0.64 cm) diameter 316 stainless steel static mixer with 21 internal helical mixer elements. To reduce decomposition of hydrogen peroxide, the assembled apparatus was cleaned in a sonic bath and subsequently passivated by submersion in a nitric acid bath.

The catalyst stream and the hydrogen peroxide stream were mixed to form one stream. The acetic anhydride stream and the acetic acid streams were mixed to form a second stream. Both streams were fed into the input section of section one. The flow rates are shown in Table 1. Water and 70% hydrogen peroxide were mixed to from a third stream, which was mixed with the stream exiting section one and fed into section two. The flow rates are shown in Table 2.

The apparatus was mounted vertically and run in an upflow manner requiring only low pressure pumps to feed the input streams. The section one input streams were provided by precise computer-controlled syringe pumps with steper motors (Kloehn Syringe Drive Module 50300, with 50 mL syringe and standard 3-way non-distribution valve, 48000 step version, Kloehn Co., Ltd., Las Vegas, Nevada). The section two input streams were provided by small calibrated pumps (FMI Model SHSY Synchronous Low Flow Drive, Fluid Metering Inc., Oyster Bay, N.Y.). Connections from the pumps and the reactor were nerally provided through 0.125 in (about 0.32 cm) Teflon® prfluorinated resin tubing and Teflon® perfluorinated resin tees. The apparatus is open to the atmosphere and can degas wihout any pressure buildup.

Stream 5, the mixture exiting section two, was collected analyzed by the procedure described in the Comparative Example. The results are presented in Table 3.

Experiments 1–6 illustrate the effect of change in residence time, at constant ratio of acetic anhydride to acetic acid. Experiments 7–12 illustrate the effect of a change in the ratio of acetic anhydride to acetic acid, at an essentially constant residence time. Experiment 6 and Exeriment 9 are the same experiment. In each experiment the same total amount of water, hydrogen peroxide, acetate, and catalyst was added.

TABLE 1

| | | | Section One | | |
|---|---|---|---|---|---|
| Exp. # | Temp (° C.) | AA (mL/min) | HOAc (mL/min) | $H_2O_2$[a] (mL/min) | 2010[b] (mL/min) | Res. Time (min) |
| 1 | 40 | 0.092 | 0.023 | 0.063 | 0.008 | 30.06 |
| 2 | 40 | 0.138 | 0.034 | 0.095 | 0.013 | 20.04 |
| 3 | 40 | 0.184 | 0.046 | 0.126 | 0.017 | 15.03 |
| 4 | 40 | 0.231 | 0.057 | 0.158 | 0.021 | 12.03 |
| 5 | 40 | 0.277 | 0.068 | 0.189 | 0.025 | 10.02 |
| 6 | 40 | 0.369 | 0.091 | 0.219 | 0.033 | 7.52 |
| 7 | 40 | 0.430 | 0.017 | 0.219 | 0.033 | 7.66 |
| 8 | 40 | 0.397 | 0.057 | 0.219 | 0.033 | 7.58 |
| 9 | 40 | 0.369 | 0.091 | 0.219 | 0.033 | 7.52 |
| 10 | 40 | 0.323 | 0.147 | 0.219 | 0.033 | 7.41 |
| 11 | 40 | 0.287 | 0.191 | 0.219 | 0.033 | 7.33 |
| 12 | 40 | 0.258 | 0.225 | 0.219 | 0.033 | 7.26 |

[a]70% Hydrogen peroxide.
[b]Dequest® 2010 stabilizer.

TABLE 2

| | Section Two | |
|---|---|---|
| Exp. # | $H_2O_2$[a] (mL/min) | Water (mL/min) |
| 1 | 0.213 | 0.521 |
| 2 | 0.319 | 0.781 |
| 3 | 0.426 | 1.041 |
| 4 | 0.532 | 1.301 |
| 5 | 0.638 | 1.562 |
| 6 | 0.851 | 2.082 |
| 7 | 0.851 | 2.094 |
| 8 | 0.851 | 2.088 |
| 9 | 0.851 | 2.082 |
| 10 | 0.851 | 2.073 |
| 11 | 0.851 | 2.067 |
| 12 | 0.851 | 2.061 |

[a]70% Hydrogen peroxide.

TABLE 3

| | Composition | | | | | |
|---|---|---|---|---|---|---|
| Exp. | $H_2O_2$ (wt %) | | PAA (wt %) | | DAP (wt %) | |
| # | Init[a] | +1 day[b] | Init | +1 day | Init | +1 day |
| 1 | 15.72 | 16.01 | 5.93 | 5.25 | 0.10 | 0.04 |
| 2 | 18.15 | 18.30 | 5.47 | 5.21 | 0.06 | 0.04 |
| 3 | 21.02 | 20.72 | 4.98 | 5.20 | 0.17 | 0.12 |
| 4 | 20.49 | 19.95 | 4.76 | 5.27 | 0.62 | 0.15 |
| 5 | 20.90 | 20.31 | 4.70 | 5.18 | 0.44 | 0.23 |
| 6 | 20.75 | 21.00 | 4.82 | 5.44 | 0.18 | 0.16 |
| 7 | 20.51 | 20.65 | 5.40 | 5.48 | 0.18 | 0.10 |
| 8 | 20.78 | 20.44 | 5.25 | 5.45 | 0.27 | 0.17 |
| 9 | 20.75 | 21.00 | 4.82 | 5.44 | 0.18 | 0.16 |
| 10 | 21.06 | 20.43 | 4.48 | 5.27 | 0.70 | 0.37 |
| 11 | 21.55 | 21.21 | 4.03 | 5.01 | 0.75 | 0.17 |
| 12 | 22.36 | 22.05 | 3.65 | 4.36 | 0.67 | 0.39 |

[a]Measured immediately after reaction.
[b]Measured about 24 hours after reaction.

Having described the invention, we now claim the owing and their equivalents.

I claim:

1. A rapid process for the production of a dilute, aqueous solution of a lower organic peracid, the process comprising:

(a) preparing a mixture comprising an anhydride corresponding to the lower organic peracid, hydrogen peroxide, water, an acid catalyst, and optionally the organic acid corresponding to the lower organic peracid;

(b) allowing the mixture to react for about 60 minutes or less; and (c) diluting the mixture with water, with hydrogen peroxide, and, optionally, with the organic acid to produce the dilute, aqueous solution;

wherein:

the amounts of anhydride, organic acid, hydrogen peroxide, and water used in steps (a) and (c) are effective to produce a predetermined, equilibrium concentration of the peracid;

the dilute, aqueous solution comprises about 0.5 wt % to about 15 wt % of peracid;

the concentration of the lower organic peracid in the dilute, aqueous solution produced in step (c) is about the predetermined, equilibrium concentration; and the hydrogen peroxide used in step (a) is 50 wt % to 90 wt % hydrogen peroxide in water.

2. The process of claim 1 in which all the anhydride is added in step (a).

3. The process of claim 1 in which the catalyst is an organic phosphonic acid.

4. The process of claim 1 in which the process is a continuous process.

5. The process of claim 1 in which the process is a batch process.

6. The process of claim 1 in which the dilute, aqueous solution comprises about 0.5% to about 7% by weight peracid.

7. The process of claim 1 in which the lower organic peracid is peracetic acid.

8. The process of claim 7 in which the dilute, aqueous solution comprises about 0.5% to about 7% by weight peracid.

9. The process of claim 8 in which the ratio of moles of organic acid equivalents to moles of hydrogen peroxide is 1.4 to 1.8.

10. The process of claim 9 in which all of the acetic anhydride is added in step (a).

11. The process of claim 9 in which the catalyst is an organic phosphonic acid.

12. The process of claim 11 in which the dilute, aqueous solution comprises about 5.0% to about 5.5% by weight peracid.

13. The process of claim 11 in which the process is a continuous process.

14. The process of claim 11 in which the process is a batch process.

15. The process of claim 11 in which the hydrogen peroxide added in step (a) is about 70% by weight aqueous hydrogen peroxide.

16. The process of claim 15 in which the dilute, aqueous solution comprises about 5.0% to about 5.5% by weight peracid.

17. The process of claim 16 in which all of the anhydride is added in step (a).

18. The process of claim 17 in which the mixture is allowed to react for 30 minutes or less.

19. The process of claim 18 in which the temperature in step (b) is between about 30° C. and 50° C.

20. The process of claim 19 in which the process is a continuous process.

21. The process of any one of claims 1–18 or 20 wherein step (b) is carried out at a temperature of about 60° C. or less.

\* \* \* \* \*